US00PP25874P3

(12) United States Plant Patent
Probasco et al.

(10) Patent No.: US PP25,874 P3
(45) Date of Patent: Sep. 8, 2015

(54) HOP PLANT NAMED 'HBC 291'

(50) Latin Name: *Humulus lupulus*
Varietal Denomination: HBC 291

(75) Inventors: Eugene G. Probasco, Yakima, WA (US); Jason Perrault, Selah, WA (US)

(73) Assignee: Hop Breeding Company, LLC., Yakima, WA (US)

( * ) Notice: Subject to any disclaimer, the term of this patent is extended or adjusted under 35 U.S.C. 154(b) by 185 days.

(21) Appl. No.: 13/385,142

(22) Filed: Feb. 3, 2012

(65) Prior Publication Data

US 2012/0278959 P1 Nov. 1, 2012

Related U.S. Application Data

(60) Provisional application No. 61/462,788, filed on Feb. 7, 2011.

(51) Int. Cl.
*A01H 5/00* (2006.01)
*A01H 5/12* (2006.01)

(52) U.S. Cl.
USPC ..... Plt./236
CPC ..... *A01H 5/12* (2013.01)

(58) Field of Classification Search
USPC ..... Plt./236
CPC ..... A01H 5/12; A01H 5/00
See application file for complete search history.

*Primary Examiner* — Kent L Bell
(74) *Attorney, Agent, or Firm* — Ballew Law

(57) ABSTRACT

A new hop plant named 'HBC 291' is disclosed. The cones of 'HBC 291' mature in mid September, and yield a crop of 2000 to 2400 pounds per acre. 'HBC 291' is used for its unique aromatic and flavor qualities, high alpha acid content and exceptional yield.

2 Drawing Sheets

Genus and species: *Humulus lupulus.*
Variety denomination: 'HBC 291'.

STATEMENT REGARDING FEDERALLY SPONSORED RESEARCH OR DEVELOPMENT

None

BACKGROUND OF THE INVENTION

'HBC 291' is a product of a controlled breeding program carried out by the inventors in the Yakima Valley of Washington state. 'HBC 291' was one of several seedlings resulting from a cross made in 2002 of female parent 'Glacier' (not patented) and male parent 'HBC 9902(2)' (not patented). A single plant of 'HBC 291' was selected in 2003, and in 2004 was expanded by softwood cutting propagation in Yakima, Wash. to 70 plants, which were then planted in the area of Toppenish, Wash. The plants were observed and evaluated for several years, and in 2009 were expanded by softwood cuttings for further observation and evaluation in the Toppenish, Wash. area. A one acre test plot of 'HBC 291' was established in 2009. Throughout several generations of asexual propagation by softwood cuttings, 'HBC 291' has been observed to retain its distinctive characteristics and remain true to type. 'HBC 291' is distinguished from other known hop cultivars by its low cohumulone and its large number of small, tight cones. 'HBC 291' has a distinctive citrus/floral aromatic property.

'HBC 291' is distinguishable from its parent plants ('Glacier' and 'HBC 9902(2)'). 'HBC 291' is distinguishable from its male parent 'HBC 9902(2)' with flowers that develop into mature hop cones without producing pollen, while flowers of 'HBC 9902(2)' produce pollen without developing into mature hop cones.

TABLE 1. sets forth some of the distinguishing characteristics of 'HBC 291' as compared to its female parent 'Glacier' and 'HBC 394' (U.S. Plant Patent 21,289):

| | 'HBC 291' | 'Glacier' | 'HBC 394' |
|---|---|---|---|
| Alpha Acids % | 10.0% to 12.0% | 3.3% to 9.7% | 11% to 13% |
| Beta Acids % | 4.5% to 5.5% | 5.4% to 9.7% | 3.5% to 4.5% |
| Cohumulone % | 21.0% to 23.0% | 11% to 13% | 22% to 24% |
| Total oils | 1.5 to 2.5 mL/ 100 g cones | 0.7 to 1.6 mL/ 100 g cones | 2.2 to 2.8 mL/ 100 g cones |

BRIEF DESCRIPTION OF THE PHOTOGRAPH

Figure 1:
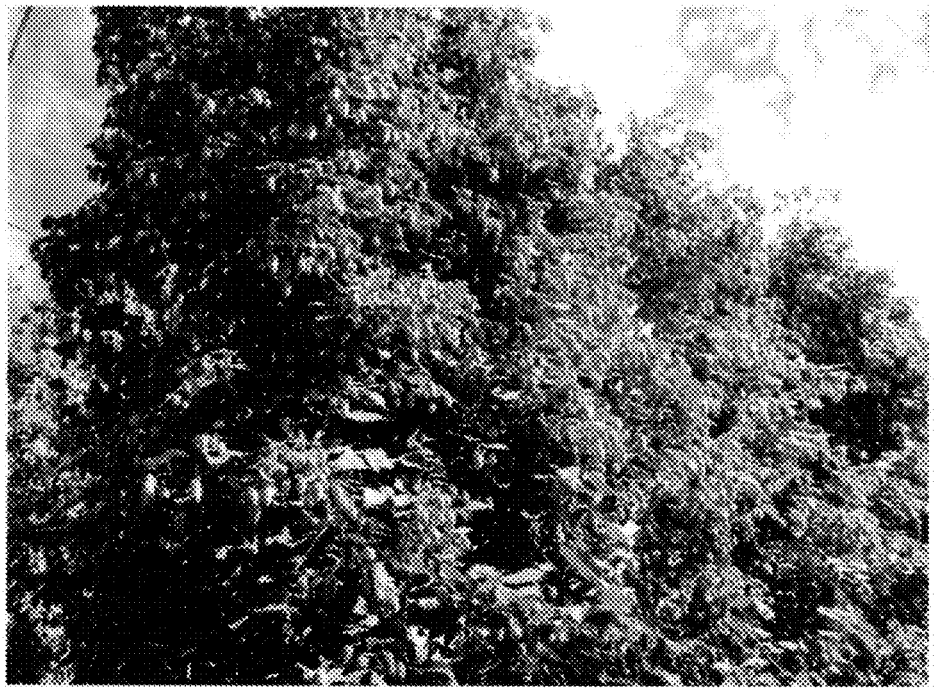
Figure 2:
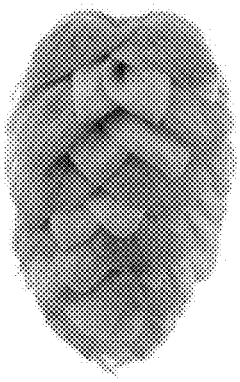

FIG. 1 illustrates a mature 'HBC 291' hop plant grown on a trellis;

FIG. 2. illustrates a hop cone of the 'HBC 291' hop plant; and

Figure 3:
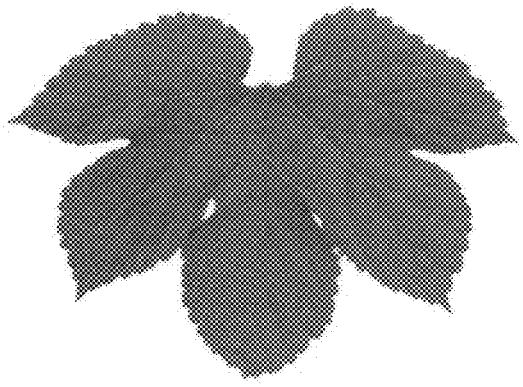

FIG. 3. illustrates a leaf of the 'HBC 291' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2011 growing season at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average.

Color code designations are by reference to The R.H.S. Colour Chart, 4th ed., Copyright 2001, provided by The Royal Horticultural Society of Great Britain.

Species: *Humulus lupulus*.

Ploidy: Diploid.

Use: Brewing.

Disease susceptibility: 'HBC 291' is not resistant to hop downy mildew. 'HBC 291' is resistant to powdery mildew.

Pest susceptibility: 'HBC 291' is not resistant to normal infestations of hop aphid and normal infestations of two-spotted spider mite.

Harvest date: September 10-16 (2006-2009, and 2011 growing seasons, Toppenish, Wash.).

Crop yield: 2000 to 2400 pounds per acre.

Plant shape: Columnar when grown on a typical 18 foot hop trellis.

Bine:

*Color*.—Yellow green 145A.
*Stipule direction*.—Reflexed.
*Stipule color*.—Yellow green 144B.
*Stripe*.—Absent.
*Bine diameter*.—10.0 mm at base; 9.0 mm at 9 feet; 8.0 mm at 18 feet.
*Bine length*.—18 to 22 feet average length when grown under normal commercial conditions on a standard hop trellis.
*Length between internodes*.—205 to 215 mm average.
*Lateral length*.—50 cm to 140 cm, with an average of 80 cm.
*Lateral diameter*.—4 mm at the base; 0.5 mm at the terminal end.
*Lateral color*.—Yellow green 148C.

Leaf:

*Arrangement*.—Opposite.
*Shape*.—Cordate; Palmate lobes.
*Leaf base shape*.—Cordate.
*Average length of mature leaf*.—24.0 cm.
*Average width of mature leaf*.—19.0 cm.
*Color of mature leaf upper surface*.—Yellow green 135A.
*Color of mature leaf lower surface*.—Green 135A.
*Color of immature leaf upper surface*.—Green 136A.
*Color of immature leaf lower surface*.—Green 136B.
*Number of lobes*.—5.
*Margin*.—Lobed Serrate.
*Serrations per inch*.—4.
*Average petiole length* (*mature*).—9.0 cm.
*Petiole diameter*.—3.0 mm at base to 2.0 mm at terminal end.
*Petiole color at base*.—Yellow green 145A.
*Petiole color at terminal end*.—Yellow green 146D.
*Petiole stripe*.—Present but diffuse for entire length, Red purple 59A.
*Venation*.—Palmate.
*Vein color*.—Yellow green 144C.

Cone:

*Average weight*.—1030 mg.
*Average length*.—3.5 cm.
*Average diameter*.—2.0 cm.
*Bract tip color*.—Yellow green 143D.
*Bract base color*.—Yellow green 143C.
*Bracteole color*.—Yellow green 149D.
*Cone shape*.—Oblong.
*Bract shape*.—Ovate.
*Bract average length*.—11 mm.
*Bract average width*.—9 mm.
*Bract tip shape*.—Cuspidate.
*Bract tip position*.—Appressed.
*Bracteole shape*.—Acute.
*Bracteole average length*.—12 mm.
*Bracteole average width*.—7 mm.
*Lupulin gland color*.—Yellow green 154B.
*Lupulin gland shape*.—Pedunculated oblong polyps.
*Lupulin gland number*.—Medium number per cone.
*Pickability*.—Good.
*Cone storage*.—30% loss of soft resins after 6 month storage at room temperature.

Analytical characteristics:

*Alpha acid*.—10.0% to 12.0%.
*Beta acid*.—4.5% to 5.5%.
*Cohumulone*.—21.0% to 23.0%.
*Myrcene*.—37.0% to 39.0%.
*Humulene*.—23.0% to 25.0%.
*Caryophyllene*.—7.0% to 9.0%.
*Farnesene*.—0.6% to 0.8%.
*Linalool*.—1.0% to 1.5%.
*Geraniol*.—0.8% to 1.1%.
*Humulene/caryophyllene ratio*.—2.8% to 3.2%.
*Total oil*.—1.5 to 2.5 mL per 100 g hops.
*Storageability*.—70% to 72% alpha acids remaining after 6 months storage at room temperature.

What is claimed is:

1. A new and distinct hop plant as shown and described herein.

* * * * *